US008703171B2

(12) United States Patent
Schaub

(10) Patent No.: US 8,703,171 B2
(45) Date of Patent: Apr. 22, 2014

(54) METHOD FOR EASING HUMAN CHILDBIRTH USING A LUBRICANT COMPOSITION

(75) Inventor: Andreas F. Schaub, Walchwil (CH)

(73) Assignee: HCB Happy Child Birth Holding AG, Walchwil (CH)

( * ) Notice: Subject to any disclaimer, the term of this patent is extended or adjusted under 35 U.S.C. 154(b) by 595 days.

(21) Appl. No.: 11/718,995

(22) PCT Filed: Nov. 10, 2005

(86) PCT No.: PCT/EP2005/012058
§ 371 (c)(1),
(2), (4) Date: May 10, 2007

(87) PCT Pub. No.: WO2006/050951
PCT Pub. Date: May 18, 2006

(65) Prior Publication Data
US 2008/0103214 A1  May 1, 2008

(30) Foreign Application Priority Data

Nov. 11, 2004 (DE) .......................... 10 2004 054 552

(51) Int. Cl.
*A61K 9/06* (2006.01)
*A61K 9/02* (2006.01)
*A61K 31/00* (2006.01)
*A61K 31/74* (2006.01)
*A61K 31/717* (2006.01)
*A61K 9/00* (2006.01)

(52) U.S. Cl.
CPC ............ *A61K 9/0034* (2013.01); *A61K 9/0036* (2013.01); *A61K 9/0024* (2013.01); *A61K 9/02* (2013.01)
USPC ........ 424/430; 424/433; 424/78.02; 424/484; 424/486; 424/487; 424/434; 424/488

(58) Field of Classification Search
None
See application file for complete search history.

(56) References Cited

U.S. PATENT DOCUMENTS

| | | | |
|---|---|---|---|
| 3,814,797 A | 6/1974 | Kasahara et al. | |
| 3,971,848 A | 7/1976 | Kasahara et al. | |
| 4,184,974 A * | 1/1980 | Van Leuven | 424/618 |
| 4,267,168 A * | 5/1981 | Van Leuven | 424/75 |
| 4,615,697 A | 10/1986 | Robinson | |
| 4,652,446 A | 3/1987 | Dettmar | |
| 4,765,478 A | 8/1988 | Bringloe | |
| 4,859,242 A | 8/1989 | Hughes et al. | |
| 4,981,686 A | 1/1991 | Hardy et al. | |
| 5,051,253 A | 9/1991 | Lloyd-Jones et al. | |
| 5,338,815 A * | 8/1994 | Aizawa et al. | 508/268 |
| 5,342,617 A | 8/1994 | Gold | |
| 5,580,574 A | 12/1996 | Behl | |
| 5,599,534 A | 2/1997 | Himmelstein et al. | |
| 5,624,903 A | 4/1997 | Muller | |
| 5,877,209 A | 3/1999 | Yunis | |
| 5,885,591 A | 3/1999 | Ahmad et al. | |
| 5,886,054 A | 3/1999 | Van Nieuw Amerongen et al. | |
| 6,139,848 A | 10/2000 | Ahmad et al. | |
| 6,217,885 B1 | 4/2001 | Roder | |
| 6,596,777 B1 | 7/2003 | Schiraldi et al. | |
| 2001/0014711 A1 | 8/2001 | Levy | |
| 2002/0012674 A1 | 1/2002 | Saettone et al. | |
| 2002/0061864 A1 | 5/2002 | Livingston et al. | |
| 2003/0091644 A1 | 5/2003 | Bologna et al. | |
| 2003/0092776 A1 * | 5/2003 | Ron et al. | 514/772.6 |
| 2003/0114394 A1 | 6/2003 | Levine et al. | |
| 2004/0209844 A1 * | 10/2004 | Scheele et al. | 514/58 |
| 2005/0031547 A1 * | 2/2005 | Tamarkin et al. | 424/45 |
| 2005/0053670 A1 | 3/2005 | Schaub | |
| 2005/0181057 A1 * | 8/2005 | Rosenberg et al. | 424/488 |
| 2007/0280891 A1 * | 12/2007 | Tamarkin et al. | 424/47 |

FOREIGN PATENT DOCUMENTS

| | | |
|---|---|---|
| GB | 1364130 | 8/1974 |
| JP | 4624256 B2 | 7/1971 |
| JP | 61195196 A | 8/1986 |
| JP | 2002029993 A | 1/2002 |
| RU | 2177789 C2 | 1/2002 |
| WO | 9209256 A1 | 6/1992 |
| WO | 93/15728 A1 | 8/1993 |
| WO | 0030629 A2 | 6/2000 |
| WO | 0174359 | 10/2001 |
| WO | 03066020 A | 8/2003 |

OTHER PUBLICATIONS

JP 8-217680 Machine translation (Kanamaru).*
JP 63218617 (abstract) (Yoneda).*
Polyethylene Glycol OECD SIDS Initial Assessment Report for 11th SIAM (Jan. 2001).*
Frazer et al., Systemic Effects of a Polyethylene Polymer-Based Obstetrical Lubricant in the Peritoneal Cavity of the Horse, AAEP Proceedings, 2004, 484-487, vol. 50.
Obst et al., Geburtensimulator mit multimodaler Interaktion (Delivery Simulator with Multimodal Interaction), Automatisierungstechnik, 2004, 280-287, vol. 6.
Albers et al.: "Factors related to perineal trauma in childbirth", Journal of Nurse-Midwifery, vol. 41, No. 4, 1996, pp. 269-276.
Albers et al.: "Midwifery care measures in the second stage of labor and reductioin of genital tract trauma at birth: A randomized trial", Journal of Midwifery Womens Health, vol. 50, No. 5, 2005, pp. 365-372.
HCB Swiss Study 2005 to 2007: randomized prospective trial with active control at three Swiss Obstetrics Dept., 2009, HCB Happy Child Birth Foundation, 6 pgs.

(Continued)

*Primary Examiner* — Kevin S Orwig
(74) *Attorney, Agent, or Firm* — Rothwell, Figg, Ernst & Manbeck, P.C.

(57) ABSTRACT

The present invention relates to a method of easing childbirth using a composition having a lubricant effect for use in particular during human vaginal delivery. The methods comprise applying a bioadhesive composition comprising (a) a polyacrylic acid, (b) a water-soluble thickener and (c) a humectant and (d) optionally water.

21 Claims, No Drawings

(56) References Cited

OTHER PUBLICATIONS

Kuhnert et al.: "Dianatal Obstetric Gel" Scientific Expert Report, 2011, pp. 1-12.
Facchinetti et al., "Chemical ripening of the cervix with intracervical application of sodium nitroprusside: a randomized controlled trial", Human Reproduction, 2000, 2224-2227, 15 (10).
Jacques et al., An investigation of the physical behaviour of moisture-activated mucoadhesive hydrogels upon contact with biological and non-biological substrates, Pharmaceutica Acta Helvetiae, 72, 1997, 225-232, et al.
Lydon-Rochelle, et al., "Perineal outcomes and nurse-midwifery management", Journal of Nurse-Midwifery, 1995, 13-18, 40(1).
Sears et al. "Perineal Massage", 1998, XP002398417, URL:http://www.childbirth.org/articles/massage.html.
Stamp et al. "Perineal massage in labour and prevention of perineal trauma:randomised controlled trial", 2001, BMJ, 1277-1280, 322.
Database WPI, Week 197127, Derwent Publications Ltd., London, Great Britian; AN 1971-46344s XP002245736 & JP 46 0242568 (Showa Yakuhin Kako KK) abstract.
Database WPI, Week 197003, Derwent Publications Ltd., London, Great Britian; AN 1970-04388r XP002245737 & JP 45 000153B (Showa Yakuhin Kako KK) abstract.
Database WPI, Week 197003, Derwent Publications Ltd., London, Great Britian; AN 1970-04387r XP002245738 & JP 45 000152B (Showa Yakuhin Kako KK) abstract.
Soranus, Soranus' Gynecology, 1956, 72-73, Johns Hopkins University Press, Baltimore, MD.

* cited by examiner

METHOD FOR EASING HUMAN CHILDBIRTH USING A LUBRICANT COMPOSITION

CROSS REFERENCE TO RELATED APPLICATION

This application is a 35 USC §371 National Phase Entry Application from PCT/EP2005/012058, filed Nov. 10, 2005, and designating the United States.

The present invention relates to a composition having a lubricant effect for use in particular in human vaginal delivery.

Vaginal delivery of a child is a complex process and is determined by three substantial factors: the item to be delivered (fetus, amnion, placenta), the birth canal (consisting of a bony portion and a soft-tissue tube) and the delivery forces. Various delivery forces which promote or inhibit the vaginal delivery of a human fetus are known from the scientific specialist literature. Delivery-promoting forces are in this connection the labor contractions and the force of gravity, while delivery-inhibiting forces are the stretching force of the mouth of the womb and of the birth canal. Delivery of a human child is divided into 3 phases: the dilation period, the expulsion period and the placental period. The normal duration of delivery in primiparas averages 12 hours, and in multiparas averages 8 hours. The reason for the shorter average duration of delivery in multiparas compared with primiparas is the reduced stretching force of the birth canal, because in multiparas the soft-tissue tube [inner soft-tissue duct (uterine segment—cervical canal—attached soft-tissue duct (vagina and vulva)] is thinned by the preceding vaginal deliveries. The prevailing doctrine relating to the mechanics of delivery in humans is accordingly that the stretching force of the birth canal (the force necessary to open, to stretch and to thin the birth canal) is to be regarded as a substantial force impeding delivery (Dudenhausen, Schneider, Frauenheilkunde und Geburtshilfe, Verlag De Gruyter (1994), pages 113 to 121).

In veterinary medicine, the mechanical significance for delivery of the frictional force between item to be delivered and birth canal has been known for decades. Lubrication of the birth canal to reduce the frictional force is a standard method in veterinary obstetrics (Richter, Götze; Tiergeburtshilfe, 4th edition; Verlag Paul Parey; Rechtsfragen in der Tiergeburtshilfe, page 614), and lubricants for this purpose are commercially available. Relatively large volumes of lubricants can be employed in animal delivery. This makes it possible to use liquid, aqueous compositions which serve as substitute for the lubricating amniotic fluid or the allantoic fluid in productive livestock. It is not possible to use such large volumes in human vaginal delivery for lack of practicability.

A substantial difference between delivery in animals and delivery in humans is that the role of the amniotic fluid in human delivery at term has no significant relevance in relation to lubrication of the birth canal and may on the contrary increase the resulting frictional forces. Amniotic fluid has, as an aqueous substance, little lubricant effect per se in humans. At present, vaginal deliveries in humans are mostly performed only with a chepalic presentation, where the escape of amniotic fluid during delivery must be designated negligible owing to the sealing by the head. The vernix caseosa, the only lubricant substance with the item to be delivered, is mostly no longer present at the time of delivery and anyway has only little effectiveness on the head. The use of amniotic fluid or substitute amniotic fluid for lubricating the birth canal before or during a vaginal delivery in humans is therefore not an appropriate measure for reducing the frictional forces and for easing vaginal delivery in humans.

U.S. Pat. No. 3,814,797 discloses aqueous lubricant compositions based on (A) potassium metaphosphate, (B) alginic acid, carboxymethylcellulose, carboxy-methylstarch and salts thereof and (C) the sodium salt of a weak acid, for example sodium carbonate or sodium phosphates.

U.S. Pat. No. 3,971,848 discloses a lubricant composition for mucous membranes, which comprises a mixture of fucoidin and an alginate. The composition may where appropriate be mixed with carboxymethylcellulose, sodium polyacrylate, potassium sodium polyphosphate, polyethylene oxide or the like and be employed for easing delivery.

U.S. Pat. No. 4,267,168 discloses a liquid biocidal composition which can be employed as cleaner, as surface disinfectant or as vaginal lubricant. The composition comprises lauryl diethanolamide, propylene glycol, glycerol, sodium polypectate and silver ions. It has a pH in the range of 7.2-7.8.

JP 46024256 discloses a lubricant composition which consists essentially of polyacrylate and can be employed as assisting uterine fluid in veterinary medicine.

JP 45000153 and JP 4500012 disclose a lubricant composition for assisting delivery in veterinary medicine, which comprises a salt or an ester of alginic acid and gum arabic.

JP 46034991 discloses a lubricant composition comprising polyethylene oxide powder in a liquid consisting of an organic solvent in a concentration of >80%, hydroxypropylcellulose, sodium sulfate and a detergent. The composition can be used after dilution to facilitate the extraction of a fetus in veterinary medicine.

PCT/EP03/00548 discloses the use of a physiologically acceptable organic substance for producing a composition containing no alkali metal salts of metaphosphates for use as lubricant in vaginal deliveries by women. Numerous examples of suitable, physiologically acceptable organic substances are mentioned. This invention relates to reducing the recently recognized substantial force impeding delivery, namely the frictional force between item to be delivered and birth canal through the use of a lubricant in humans.

The object on which the present invention was based was to provide a composition for easing human childbirth which is physiologically tolerated and exhibits both good adhesion properties and a lubricant effect.

This object is achieved by a bioadhesive composition having a lubricant effect, comprising (a) a polyacrylic acid, (b) a water-soluble thickener and (c) a humectant and (d) where appropriate water.

Component (a) of the composition of the invention is a polyacrylic acid which may be crosslinked or/and chemically modified, or a salt of such a polyacrylic acid or a mixture of a plurality of polyacrylic acids. The average molecular weight of the acrylic acid polymers is chosen so that they exhibit bioadhesive properties in the intended application. The molecular weight is normally in the region of at least 2000 D and preferably up to 500 000 D.

Preferred polyacrylic acids are crosslinked acrylic acid polymers, e.g. acrylic acid homopolymers, copolymers or interpolymers or salts of such polymers, e.g. alkali metal or alkaline earth metal salts. These include for example carbomer homopolymers, i.e. high molecular weight polymers of acrylic acid which are crosslinked by polyalkenyl ethers of sugars or polyalcohols, such as, for example, allylsucrose, allyl-pentaerythritol etc., e.g. Carbopol® 940 NF, 974P NF or 980 NF.

Also suitable are carbomer copolymers, i.e. high molecular weight copolymers of acrylic acid and $C_1$-$C_{24}$-alkyl methacrylates crosslinked by polyalkenyl ethers of sugars or polyalcohols, such as, for example, Carbopol® 1382, Carbopol® 1342 NF, Carbopol® ETD-2020, Pemulen® TR1 NF and Pemulen® TR2 NF. Likewise suitable are carbomer interpolymers, i.e. carbomer homopolymers or copolymers which comprise a heterologous polymer, e.g. a block copolymer of polyethylene glycol and a long-chain, e.g. $C_1$-$C_{24}$-alkyl acid ester, such as, for example, Carbopol® Ultrez 10, 20 or 21 or Carbopol® Ultrez 10 NF. Likewise suitable are polycarbophils, i.e. polyacrylic acids crosslinked by divinyl glycol, such as, for example, Noveon® AA-1 USP, or calcium polycarbophils, i.e. calcium salts of polyacrylic acid crosslinked with divinyl glycol, such as, for example, Noveon® CA-1 USP and CA-2 USP.

The polyacrylic acid homopolymers normally have a COOH group content of 56-68%, whereas the polyacrylic acid copolymers have a COOH group content of 52-62%.

The proportion by weight of component (a) in the total weight of the composition may be varied within wide limits, for example from 0.1-15%. Especially when the composition is in the form of a hydrous gel, the proportion by weight of component (a) is preferably 0.1-10%, particularly preferably 0.2-1% and even more preferably 0.4-0.7%. The proportion by weight is most preferably 0.45-0.5%.

Component (b) of the composition is a water-soluble thickener or a mixture of a plurality of thickeners. Preferred examples are cellulose derivatives, especially hydrophilically modified cellulose derivatives such as, for example, hydroxyethylcellulose, hydroxypropylcellulose, carboxymethylcellulose, or/and hydroxypropylmethylcellulose. Further preferred water-soluble thickeners are mucopolysaccharides, in particular hyaluronic acid.

Component (b) is normally present in a proportion by weight of 0.1-30%, preferably of 1-10%, particularly preferably of 2.5-7.5% and most preferably of 4-6% based on the total weight of the composition.

Component (c) of the composition is a humectant or a mixture of a plurality of humectants. Preferred examples are pharmaceutically acceptable polyalcohols such as, for example, propylene glycol, especially 1,2-propylene glycol, glycerol or/and polyethylene glycol, especially liquid polyethylene glycol.

Component (c) is normally present in a proportion by weight of 0.1-30%, preferably of 10-30%, particularly preferably of 15-25% and most preferably of 18-22% based on the total weight of the composition.

Component (d) which is optionally present in the composition is water. In hydrous compositions, the water is normally present in a proportion by weight of 40-95%, preferably of 60-85%, particularly preferably of 70-80% and most preferably of 72-77% based on the total weight of the composition. However, it is also possible where appropriate for the composition to be present and to be used in a form which has a lower water content or is dry, e.g. as powder, or/and be diluted shortly before use.

Besides the abovementioned components, the composition may comprise excipients such as, for example, surfactants, dispersants, further thickeners, reagents to establish a pH value, carriers, fillers, stabilizers or/and preservatives. However, the composition is preferably free of preservatives. It is further preferred for the composition to be free of alginic acid or alginates, because addition of these substances often leads to the formation of unwanted discolorations or precipitates. The composition is likewise preferably free of metaphosphates or/and heavy metal ions, especially silver ions. The composition preferably further comprises ethylenediaminetetraacetic acid (EDTA) or/and pharmaceutically acceptable salts thereof.

However, the composition preferably comprises means for establishing a substantially isotonic osmolarity, for example salts such as, for instance, sodium chloride in a proportion by weight normally of 0.1-5%, preferably of 0.3-0.6%, particularly preferably of 0.45-0.55% and most preferably for instance of 0.49-0.50% based on the total weight of the composition.

The composition of the invention is preferably a gel which beneficially has a substantially colorless and transparent appearance. In addition, the composition may also be in the form of solid dosage forms such as tablets, powders, pastes, suppositories, coated tablets, effervescent tablets or suspensions thereof, or else in the form of a foam. The pH of the composition is preferably adjusted to a range of 4-7, preferably of 5-6 and most preferably of 5.5-6 by adding suitable reagents, e.g. acids such as HCl or bases such as NaOH. The pH is preferably determined in this connection by potentiometry on a gel diluted 1:9 in a 1.0% $KNO_3$ solution.

The viscosity of the composition is preferably in the range of 1-40 Pa·s, particularly preferably in the range of 10-18 Pa·s. The viscosity is preferably determined in this connection using a rotational viscometer, speed series N, level 4, sensor SV DIN, time 60 s, 20 revolutions at 20° C. The viscosity can alternatively be determined using a Brookfield RVT viscometer with the spindle rotating at a speed of 0.05 to 100 revolutions per minute.

The conductivity of the composition is preferably in the range of 4-25 mS·cm$^{-1}$, particularly preferably of 8-12 mS·cm$^{-1}$, determined with a conductivity meter, e.g. the Konduktor 702 from Knick, as specified in DIN 61326/A1/VDE 0843 part 20/A1.

The composition beneficially has thixotropic or/and pseudoplastic properties, with the viscosity decreasing under the influence of increasing shear stress or/and shear rate. The composition moreover preferably has a high initial shear stress or/and a pseudoplastic behavior, i.e. the adhesion of the composition decreases under the influence of increasing shear load.

The composition may be in sterile form, in which case for example a steam sterilization or/and a sterilization by irradiation, e.g. by gamma irradiation, is possible. However, the composition may likewise be employed in non-sterilized form or/and comprise preservatives or/and biocidal substances.

The production of the composition preferably includes the following steps:
(i) preparation of a first mixture of polyacrylic acid (a) and water (d), where appropriate with adjustment of the toxicity, e.g. by adding NaCl, or/and of the pH, e.g. by adding a base such as NaOH, the first mixture preferably being in the form of a gel,
(ii) preparation of a second mixture of a water-soluble thickener (b), of a humectant (c) and water (d), the second mixture preferably being in the form of a gel,
(iii) combining the two mixtures,
(iv) where appropriate homogenization and
(v) where appropriate sterilization.

The process or individual steps thereof can be varied depending on the pharmaceutical form intended for the composition, or on additives which are possibly present. Thus, for example, water or/and humectant can be at least partly removed or/and added during the process.

The composition is preferably in the form of packaged dosage units in a volume of 5-500 ml, particularly preferably in packaged dosage units in a volume of 10-20 ml. The composition is moreover advantageously in a packaging, for example jars, syringes, e.g. disposable syringes, or tubes, or it can be used as vaginal suppository. A further possibility is to employ a vaginal applicator. When jars are used, the composition can be applied using the fingers or spatulas to the surface of the birth canal. Tubes or syringes are more expedient, it being possible to apply the composition from them to the surface of the birth canal by pressure. The size of the packaging can be chosen so that the amount of the composition is sufficient for a single application. The tubes or syringes can be provided with an extension which substantially corresponds to the length of the birth canal and to the end of which the orifice for emergence of the composition is attached. The orifice for emergence is expediently designed, for example as round aperture, so that the composition can be completely and substantially uniformly distributed on the surface of the birth canal.

Use of the composition to be used according to the invention is simple and effective when the composition is applied before onset of regular labour contractions, in the dilation phase or/and in the expulsion phase. Application can take place one or more times. Application shortly before or during the dilation phase may have the advantage that the tissue in the birth canal is softened, additionally facilitating delivery. The composition can likewise also be employed to facilitate removal of the placenta.

In a preferred embodiment, the composition may additionally comprise one or more active pharmaceutical ingredients which serve as medicaments for certain indications occurring during delivery, e.g. delivery-inhibiting or delivery-promoting agents, agents to alleviate pain or/and agents to prevent infections. The amount of active pharmaceutical ingredients can be for example 0.0001-50% by weight, preferably 0.01-10% by weight and particularly preferably 0.01-5% by weight, based on the total weight of the composition.

Some examples of delivery-inducing substances are oxytocin, dinoprostone, sulprostone, misoprostol and hyaluronidase.

Some examples of delivery-inhibiting substances are chondroitin sulfate, hexoprenaline, fenoterol, magnesium sulfate, atosiban, calcium antagonists and nitroglycerin.

Some examples of analgesic substances are bupivacaine, Carbostesin, lidocaine, mepivacaine, Rapidocaine, Scandicaine, Solarcaine and Xylesin.

Some examples of antiinfectious agents and biocidal substances are antibacterial or/and antimicrobial or/and antiviral substances, such as quaternary ammonium compounds, chlorhexidine, povidone-iodine and iodine, and iodine-containing compounds.

It is particularly advantageous to admix antiviral substances, e.g. to prevent the transmission of herpes or HIV from the mother to the child, e.g. nucleoside analogs, nucleosidic reverse transcriptase inhibitors, non-nucleosidic reverse transcriptase inhibitors and protease inhibitors.

It is likewise particularly advantageous to admix antibacterial substances, e.g. to prevent transmission of streptococci, e.g. type B streptococci, from the mother to the child, e.g. chlorhexidine.

It has also proved expedient to admix pulmonary surface-active substances (pulmonary surfactants), with which the respiratory activity of the neonate after delivery can be facilitated, e.g. colfosceril palmitate, Lucinactant, Beractant, phospholipida e pulmone suis, perfluorocarbons.

The composition is particularly suitable as lubricant for easing human vaginal childbirth or/and for facilitating removal of the placenta. It can be applied before or/and after the start of regular labour contractions one or more times as required. Application preferably takes place in the birth canal including mouth of the womb. Intraamniotic application may likewise be expedient.

It is possible by use of the composition for human childbirth to be considerably eased and even reduced in duration, especially in primiparas when the walls of the mouth of the womb or/and vagina (birth canal) are covered with the lubricant before or/and during delivery. It is possible thus possible for the friction between birth canal and item to be delivered to be greatly reduced both in the dilation period and in the expulsion period. It is additionally possible to reduce or preclude the risk of injuries (such as, for example, thinning of the attached soft tissue duct, pelvic floor damage, vaginal tears, perineal injuries, rectal injuries, uterine ruptures, blood loss) and for long-term damage such as, for example, urinary incontinence, fecal incontinence, sexual dysfunction and psychological disturbances, to be restricted or prevented. Moreover, the work of delivery can be reduced due to the low friction, possibly leading to an avoidance or reduction in vaginal surgical procedures or caesarian sections. Manual removal of the placenta can also be facilitated by the lubricant of the invention.

It is preferable for the delivery gel to be removed from the package while maintaining sterile conditions before use. During the delivery process, the gel is then applied one or more times intermittently to the birth canal by using the hand or another aid until the child's head is delivered. The aim in this case is for the birth canal to be covered as completely as possible with the lubricant gel. After the child's head has been delivered, the gel on the child's face can be wiped off with a cloth and, where appropriate, suction can additionally be applied to the mouth-nose region. Complete delivery of the child ideally takes place with the aid of a cloth, so that the child does not slip out of the hands.

After delivery of the child or/and after delivery of the placenta, the birth canal is rinsed with an aseptic aqueous solution, preferably with a mild aseptic aqueous salt solution, so that the lubricant gel is dissolved. This can take place during or independently of the management of injuries to the perineum or the birth canal. The lubricant gel can, where appropriate, additionally be employed for facilitating the delivery of the placenta or manual removal of the placenta. The procedure in the management of a breech presentation delivery is analogous with adaptations.

The present invention is further explained by the following examples:

EXAMPLES

A Formulation Examples

Formulation Example 1

| | |
|---|---|
| sodium chloride: | 4.95 mg/g |
| propylene glycol: | 200.00 mg/g |
| Carbopol ® 940: | 4.85 mg/g |
| hydroxyethylcellulose (Natrosol 250 G): | 45.00 mg/g |
| purified water: | 745.20 mg/g |

Formulation Example 2

| | |
|---|---|
| sodium chloride: | 4.95 mg/g |
| sodium hydroxide (5N): | 2.00 mg/g |
| propylene glycol: | 200.00 mg/g |
| Carbopol ® 980 NFL | 4.85 mg/g |
| hydroxyethylcellulose (Natrosol 250 G) | 45.00 mg/g |
| purified water: | 743.20 mg/g |

Formulation Example 3

| | |
|---|---|
| sodium chloride: | 0.495% (m/m) |
| propylene glycol: | 20.0% (m/m) |
| hydroxyethylcellulose (Natrosol 250 M): | 2.5% (m/m) |
| Carbopol ® 980 NF: | 0.485% (m/m) |
| sodium hydroxide (5N) | 0.85% (m/m) |
| purified water: | 75.67% (m/m) |

Formulation Example 4

| | |
|---|---|
| sodium chloride: | 4.95 mg/g |
| propylene glycol: | 200.00 mg/g |
| Noveon AA-1 USP polycarbophil: | 4.85 mg/g |
| hydroxyethylcellulose (Natrosol 250 G): | 45.00 mg/g |
| purified water: | 745.20 mg/g |

Formulation Example 5

| | |
|---|---|
| sodium chloride: | 4.95 mg/g |
| sodium hydroxide (5N): | 2.00 mg/g |
| propylene glycol: | 200.00 mg/g |
| Noveon AA-1 USP polycarbophil: | 4.85 mg/g |
| hydroxyethylcellulose (Natrosol 250 G): | 45.00 mg/g |
| purified water: | 743.20 mg/g |

Formulation Example 6

| | |
|---|---|
| sodium chloride: | 0.495% (m/m) |
| propylene glycol: | 20.0% (m/m) |
| hydroxyethylcellulose (Natrosol 250 M): | 2.5% (m/m) |
| Noveon AA-1 USP polycarbophil: | 4.85 mg/g |
| sodium hydroxide (5N) | 0.85% (m/m) |
| purified water: | 75.67% (m/m) |

The products of the above examples are clear, almost odorless and almost colorless transparent viscous gels having the following properties:
pH 5.5-6.0
viscosity: about 10-18 Pa·s (rotational viscometer) (Pa·s=Pa×s)
density: 1.032-1.042 g/cm$^3$
conductivity: 8.0-12.0 mS·cm$^{-1}$
refractive index $n_D^{20}$: 1.361 (1.26-1.46)

water-binding capacity: high
mucoadhesiveness: high
pH determination: The pH is determined by potentiometry using a suitable pH-meter. A 10% solution of the gel in a 1.0% $KNO_3$ solution is used for the measurement.

Viscosity determination: The viscosity is determined using a rotational viscometer (instrument and measuring parameters: speed series N/level 4/sensor SV DIN/time 60 s/20 revolutions/min). All measurements take place at 20° C.

Density: The density is determined using a pycnometer or using another equally suitable instrument. The formula used for calculation is $$\delta_{20°C.} = m \cdot 0.99703 + 0.0012 (g/cm^3) \delta$$

M=mass of the liquids to be investigated, weighed in air
W=mass of the same volume of water, weighed in air
Both volumes must be measured at 20° C.
Conductivity: The conductivity is measured using a conductivity meter complying with DIN 61326A1/VDE 0843 part 20/A1.

B Production Example

Production of 10 kg for Packaging in 1000 Syringes Each Containing 10 g

Firstly, 49.5 g of sodium chloride are completely dissolved in 500 g of water in a homogenizer (Tornado ET21). Then 48.5 g of polyacrylic acid (Carbopolum® 940) and 2000 g of water are added and mixed by stirring for 5 minutes. Subsequently, while stirring for 10 minutes, sufficient aqueous 10 percent NaOH is added to establish a pH between 5.5 and 5.6. The gel produced in this way (mixture 1) is stored at room temperature until processed.

450 g of hydroxyethylcellulose (hydroxyethylcellulosum H 300 p) are added to 2000 g of 1,3-propylene glycol and suspended in a stirred container. 4952 g of water are introduced into a homogenizer, and the suspension is added and then mixed and homogenized for 10 minutes. The gel-like mixture (mixture 2) is stored overnight (12 hours). Mixture 1 produced first is added to this mixture 2 and homogenized for 5 minutes.

The finished gel is slightly opaque and transparent and odorless and has a pH of from 5.5 to 6.0. The viscosity is 16 000 mPas (measured with a Haake rotational viscometer, model VT 500, speed series N, level 4, sensor SV DIN, time 60 s, 20 revolutions/min, at 20° C.).

The gel is transferred into a sterile dispensing system, and 1000 syringes are charged with 10 g of gel. The outlet of the syringe is closed with a cap, subsequently sealed in a film and then sterilized at 121° C. for 15 minutes to give the product ready for use.

C Use Examples

Example 1

Use of Lubricant for Easing the Dilation and Expulsion Periods During Childbirth in Humans A lubricant gel was used as specified in the invention in a group of 8 primiparous women. For this purpose, not only was the lubricant gel used as customary for vaginal examination; instead, the birth canal was intermittently covered manually with the lubricant. The amount of lubricant gel necessary for this was 10 to 15 times higher than on use for vaginal examination. It was possible to establish in this investigated group that the average duration of delivery was significantly shorter than the established normal values, and that vaginal delivery by the women was overall easier than in comparable primiparas without the use of a lubricant. Overall, the trauma of delivery was less for mother and child. In addition, it was unnecessary in this investigated group to perform any vaginal surgery to complete delivery, and no injuries to the birth canal, such as vaginal tears, were found.

Example 2

Use of Lubricant for Facilitating Removal of the Placenta

In a group of 5 patients with post-partum retention of the placenta, manual removal of the placenta was facilitated by applying a lubricant to the arm of the person assisting delivery and to the birth canal. It emerged from this that manual removal of the placenta could be performed more easily and quickly, and that the blood loss could be reduced thereby.

Biocompatibility Test

Test Procedure

Based on the following references, a biocompatibility test was carried out on formulation example 2 of the invention:
1. "In Vitro Fertilization and Embryo Transfer" A Manual of Basic Techniques. Ed.: Wolf, Don P., New York & London: Plenum Press, Chapter 5: Mouse Embryo Culture Bioassay, pages 57-76, 1988.
2. ISO 10993-12, 2002, Biological Evaluation of Medical Devices—Part 12: Sample Preparation and Reference Materials.
3. ISO/IEC 17025, 2005, General Requirements for the Competence of Testing and Calibration Laboratories.

In this test, two-cell mouse embryos were introduced into microtiter plate wells which contained a negative control (minimal medium (MEM)), the extract of a positive control (latex tube) or an extract of formulation example 2. Each test was carried out in duplicate with 10 embryos in each case, the embryos being kept in an incubator at a temperature of 37±1° C. for 72±2 hours.

Results

After exposure for 72 hours, no significant decrease in the number of viable mouse embryos was observed for the extract of formulation 2 of the invention compared with the negative control, while the positive control brought about a marked decrease in the number of viable mouse embryos. Taking account of these test results, formulation example 2 of the invention was categorized as non-embryotoxic.

The invention claimed is:

1. A method for reducing the frictional force between an item to be delivered and the birth canal of the mother in human vaginal child birthing, comprising applying a composition having a lubricant effect to the birth canal of the mother, the composition comprising
   (a) 0.4 to 0.7% by weight cross-linked polyacrylic acid,
   (b) 1 to 6% by weight hydroxyethyl cellulose,
   (c) 15 to 25% by weight propylene glycol, and
   (d) sodium hydroxide, water, sodium chloride, or a combination thereof, and
   wherein said composition is free of alginic acid, alginates, and silver ions.

2. The method of claim 1, wherein
   the composition is applied one or more times before or/and after the start of regular labor contractions.

3. The method of claim 1, wherein
   the composition is applied in the birth canal, where appropriate including the mouth of the womb or/and intraamniotically.

4. The method of claim 1 wherein the composition is a lubricant for facilitating removal of the placenta.

5. A method for easing human childbirth in a mother comprising applying a composition having a lubricant effect to the birth canal of the mother, said composition comprising
   (a) 0.4 to 0.7% by weight cross-linked polyacrylic acid,
   (b) 1 to 6% by weight hydroxyethyl cellulose,
   (c) 15 to 25% by weight propylene glycol, and
   (d) sodium hydroxide, water, sodium chloride, or a combination thereof, and
   wherein said composition is free of alginic acid, alginates, and silver ions.

6. The method of claim 5, wherein said composition to be applied has a pH in the range of 4-7.

7. The method of claim 5, wherein the composition to be applied has a viscosity of 1-40 Pa·s.

8. The method of claim 5, wherein the composition to be applied has thixotropic or/and pseudoplastic properties.

9. The method of claim 5, wherein the composition to be applied has a conductivity of 4-25 mS·cm$^{-1}$.

10. The method of claim 5, wherein the composition to be applied further comprises salts in a proportion by weight of approximately 0.1-5%.

11. The method of claim 5, wherein the composition to be applied is sterilized.

12. The method of claim 5, wherein the composition to be applied is free of preservatives.

13. The method of claim 5, wherein the composition to be applied is in the form of a gel, a solid dosage form, a suspension, or a foam.

14. The method of claim 5, wherein the composition to be applied additionally comprises at least one active pharmaceutical ingredient.

15. The method of claim 6, wherein the composition to be applied has a pH in the range of 5.5-6.

16. The method of claim 7, wherein the composition to be applied has a viscosity of 10-18 Pa·s.

17. The method of claim 9, wherein the composition to be applied has a conductivity of 8-12 mS·cm$^{-1}$.

18. The method of claim 5, wherein said composition comprises 0.3 to 0.6% by weight sodium chloride.

19. The method of claim 5, wherein said composition comprises no more than 22% by weight propylene glycol.

20. The method of claim 5, wherein the composition is applied at least once before the start of regular labor contractions.

21. A method for easing human childbirth in a mother comprising applying a composition having a lubricant effect to the birth canal of the mother, said composition consisting of
   (a) 0.4 to 0.7% by weight cross-linked polyacrylic acid,
   (b) 1 to 6% by weight hydroxyethyl cellulose,
   (c) 10 to 30% by weight propylene glycol,
   (d) 0.3 to 0.6% by weight sodium chloride,
   (e) an amount of sodium hydroxide sufficient to adjust the composition's pH to 5.0 to 6.0, and
   (f) water.

* * * * *